United States Patent [19]

Li et al.

[11] Patent Number: 5,078,730
[45] Date of Patent: Jan. 7, 1992

[54] HOLDER FOR SUTURE ANCHOR ASSEMBLY

[75] Inventors: Lehmann K. Li, Wellesley; John T. Rice, Lincoln; Robert P. Zoletti, Needham, all of Mass.

[73] Assignee: Mitek Surgical Products, Inc., Norwood, Mass.

[21] Appl. No.: 609,924

[22] Filed: Nov. 6, 1990

[51] Int. Cl.⁵ .............................. A61B 17/00
[52] U.S. Cl. ....................... 606/228; 206/63.3
[58] Field of Search ............ 606/148, 228; 206/63.3

[56] References Cited

U.S. PATENT DOCUMENTS

| | | | |
|---|---|---|---|
| 4,089,409 | 5/1978 | Cerwin | 606/228 |
| 4,126,221 | 11/1978 | Cerwin | 606/228 |
| 4,898,156 | 2/1990 | Gatturna et al. | 606/72 |
| 4,899,743 | 2/1990 | Nicholson et al. | 606/139 |
| 4,946,468 | 8/1990 | Li | 606/72 |
| 5,002,550 | 3/1991 | Li | 606/139 |

Primary Examiner—Stephen C. Pellegrino
Assistant Examiner—Gary Jackson
Attorney, Agent, or Firm—Pandiscio & Pandiscio

[57] ABSTRACT

A novel holder is disclosed which is adapted to be used in conjunction with a suture anchor assembly of the sort comprising at least a suture attached to a suture anchor and preferably also comprising at least one surgical needle attached to the suture, wherein the holder comprises suture anchor holding means for releasably holding the suture anchor to the holder, suture holding means for releasably holding the suture to the holder, and needle holder means for releasably holding the at least one needle to the holder, if the same is provided as part of the suture anchor assembly, and covering means for selectively covering the suture anchor while it is held by the suture anchor holding means, and for selectively covering substantially all of the suture while it is held by the suture holding means, and for selectively covering the at least one needle while the needle is held by the needle holding means, if the same is provided as part of the suture anchor assembly.

23 Claims, 2 Drawing Sheets

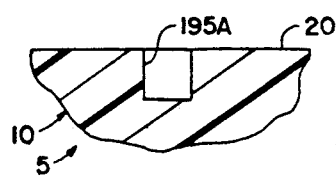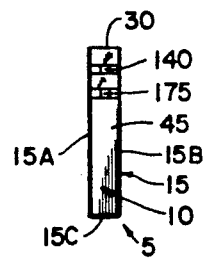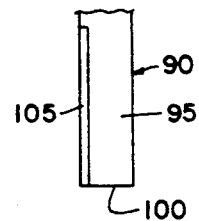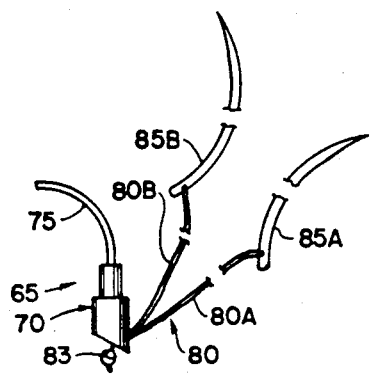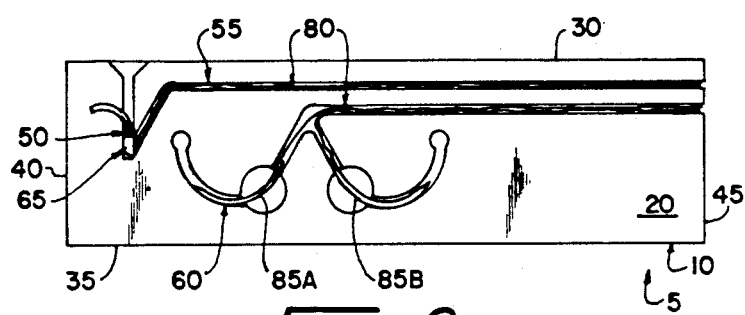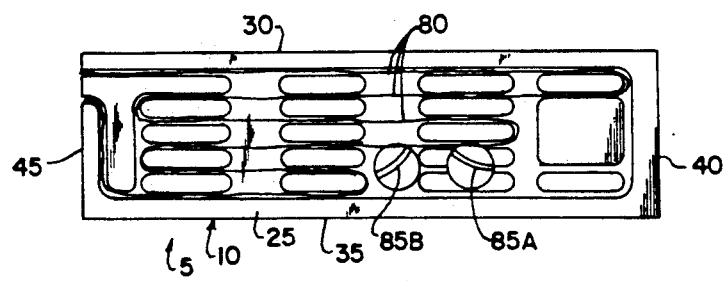

HOLDER FOR SUTURE ANCHOR ASSEMBLY

FIELD OF THE INVENTION

This invention relates generally to suture anchors of the sort adapted to anchor a portion of suture in bone, and more particularly to holders for holding suture anchors prior to deployment of the suture anchors in bone.

BACKGROUND OF THE INVENTION

Suture anchors for anchoring a portion of suture in bone, and installation tools for deploying the same, are described and illustrated in U.S. Pat. No. 4,898,156, issued Feb. 6, 1990, to Gatturna et al.; U.S. Pat. No. 4,899,743, issued Feb. 13, 1990, to Nicholson et al.; U.S. Pat. No. 4,946,468, issued Aug. 7, 1990, to Li; U.S. patent application Ser. No. 07/308,318, now U.S. Pat. No. 4,968,315, filed Feb. 8, 1989, by Gatturna; and U.S. patent application Ser. No. 07/476,307, filed Feb. 7, 1990, now U.S. Pat. No. 5,002,550, by Li, all of which are incorporated herein by reference.

Still other suture anchors and suture anchor installation tools are described and illustrated in U.S. Pat. No. 4,632,100, issued Dec. 30, 1986, to Somers et al.; U.S. Pat. No. 4,738,255, issued Apr. 19, 1988, to Goble et al.; and U.S. Pat. No. 4,741,330, issued May 3, 1988, to Hayhurst, all of which are incorporated herein by reference.

In some circumstances the suture anchor may be packaged separately from its associated installation tool; in addition, it may also be packaged separately from its associated suture, as well as packaged separately from the one or more surgical needles which are generally used in conjunction with the suture. In such a situation at least the suture anchor and installation tool, and possibly also the suture and needles, must be united in the operating room before use. See, for example, the apparatus described and illustrated in U.S. Pat. Nos. 4,898,156 and 4,899,743, and U.S. patent application Ser. No. 07/308,318. In a typical scenario using this apparatus, the suture anchor, suture anchor installation tool, suture and needles might all be packaged separately from one another. At the time of use, the suture is generally first attached to the suture anchor, then the needles are attached to the suture, and finally the suture anchor is attached to the installation tool. Only then may the installation tool be used to deploy the suture anchor in bone.

In other circumstances the suture anchor, suture, needles and installation tool may all be united with one another at the time of manufacture so as to form a complete, preassembled unit. See, for example, the apparatus described and illustrated in U.S. Pat. No. 4,946,468 and U.S. patent application Ser. No. 07/476,307. In a typical scenario using this apparatus, the preassembled unit is generally ready for use as soon as it is removed from its sterilized packaging.

The present invention is directed to situations where a suture anchor assembly, consisting of at least a suture anchor and suture, and preferably also at least one surgical needle, is preassembled prior to use, but where the suture anchor and suture anchor installation tool must be united at the time of use.

In such situations, it is important that the suture anchor be held stable while it is united with the suture anchor installation tool. In addition, it is important that the suture be kept from tangling after the suture anchor assembly has been removed from its packaging and before it is deployed in the body. Furthermore, in the situation where the suture anchor assembly comprises at least one surgical needle, it is important that the needles be kept shielded from both patient and physician once they have been removed from their protective packaging and before they are used at the surgical site.

OBJECTS OF THE INVENTION

Accordingly, the principal object of the present invention is to provide a holder in which a suture anchor assembly, comprising at least a suture attached to a suture anchor and preferably also comprising at least one surgical needle attached to the suture, can be maintained from the time of manufacture until at least after the time that the suture anchor is united with the suture anchor installation tool.

Another object of the present invention is to provide a holder which will hold the suture anchor of the suture anchor assembly and permit its position to be carefully controlled while the suture anchor is being united with the suture anchor installation tool.

Still another object of the present invention is to provide a holder which will hold the suture of the suture anchor assembly and permit it to be maintained and then deployed in a carefully controlled manner so as to prevent any tangling of the suture before it is deployed in the body.

Yet another object of the present invention is to provide a holder which will hold the at least one surgical needle of the suture anchor assembly, if one is provided as part of the suture anchor assembly, and permit it to be maintained in a protected manner until it is needed by the physician.

And another object of the present invention is to provide a holder which will hold a suture anchor assembly, comprising at least a suture attached to a suture anchor and preferably also at least one surgical needle attached to the suture, prior to unification of the suture anchor with the suture anchor installation tool, and in which the user can observe the condition of the suture anchor assembly the entire time that its components are carried by the holder.

Still another object of the present invention is to provide a holder which can be used with a variety of different suture anchors and suture anchor assemblies.

SUMMARY OF THE INVENTION

These and other objects of the present invention are addressed by a novel holder adapted to be used in conjunction with a suture anchor assembly of the sort comprising at least a suture attached to a suture anchor and preferably also comprising at least one surgical needle attached to the suture, wherein the holder comprises suture anchor holding means for releasably holding the suture anchor to the holder, suture holding means for releasably holding the suture to the holder, and needle holder means for releasably holding the at least one needle to the holder, if the same is provided as part of the suture anchor assembly, and covering means for selectively covering the suture anchor while it is held by the suture anchor holding means, and for selectively covering substantially all of the suture while it is held by the suture holding means, and for selectively covering the at least one needle while the needle is held by the needle holding means, if the same is provided as part of the suture anchor assembly.

BRIEF DESCRIPTION OF THE DRAWINGS

Still other objects and features of the present invention will be disclosed or rendered obvious by the following detailed description of the invention, which is to be considered together with the accompanying drawings wherein like numbers refer to like parts and further wherein:

FIG. 5 is a sectional view taken along line 5—5 of FIG. 1;

FIG. 6 is a rear view in elevation showing the rear of the holder;

FIG. 7 is a side view in elevation showing a typical suture anchor assembly of sort which may be used in conjunction with the holder, wherein the suture anchor assembly comprises a suture anchor, suture and a pair of surgical needles;

FIG. 8 is a side view in elevation showing a portion of a typical suture anchor installation tool of the sort which may be used in conjunction with the holder;

FIG. 9 is a view like that of FIG. 1, except that a suture anchor assembly has been seated in the holder; and FIG. 10 is a view like that of FIG. 2, except that a suture anchor assembly has been seated in the holder.

DETAILED DESCRIPTION OF THE INVENTION

Figure 1:
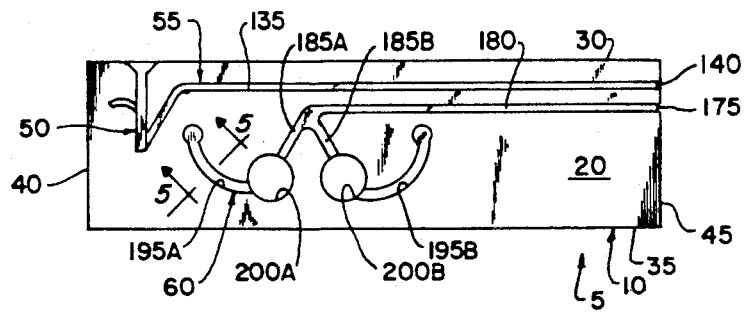
FIG. 1 is a side view in elevation showing the left side of a holder formed in accordance with the present invention.

Looking first at FIGS. 1-6, there is shown a holder 5 formed in accordance with the present invention. Holder 5 generally comprises a body 10 and a cover 15.

Body 10 comprises a generally rectangular block of material that is relatively strong and light in weight, and comprises a left side surface 20 (FIG. 1), a right side surface 25 (FIG. 2), a top surface 30 (FIG. 1), a bottom surface 35, a front surface 40 and a rear surface 45. Alternatively, body 10 may have any other suitable geometry. Body 10 may or may not be formed out of a transparent plastic.

Body 10 has its outer surfaces cut away in various locations so as to form suture anchor holding means 50 (FIG. 1) for releasably holding a suture anchor to holder 5, suture holding means 55 for releasably holding a suture to the holder, and needle holding means 60 for releasably holding a pair of surgical needles to the holder. As will hereinafter be described in further detail, suture anchor holding means 50, suture holding means 55 and needle holding means 60 comprise channels formed in the outer surfaces of body 10 which reflect the profile of the particular suture anchor assembly members they are to receive, i.e., suture anchor holding means 50 comprises at least one channel formed in the outer surface of body 10 which reflects the profile of the suture anchor which is to be received therein, suture holding means 55 comprises at least one channel formed in the outer surface of body 10 which reflects the profile of the suture which is to be received therein, and needle holding means 60 comprises at least one channel formed in the outer surface of body 10 which reflects the profile of the at least one needle which is to be received therein. In this respect it will, of course, be be appreciated that the particular geometries selected for suture anchor holding means 50, suture holding means 55 and needle holding means 60 will be determined by the particular geometries employed by the suture anchor, suture and needles which are to be received by holder 5.

By way of illustration, in the preferred embodiment of the invention it is intended that the suture anchor holding means 50 receive a suture anchor of the sort described and illustrated in U.S. patent application Ser. No. 07/308,318, and present such a suture anchor for unification with a suture anchor installation tool of the sort described and illustrated in that same application. A representative suture anchor 65, of the sort described and illustrated in U.S. patent application Ser. No. 07/308,318, is shown in FIG. 7, and generally comprises a body member 70 and a barb member 75. A suture 80, having two ends 80A and 80B and a knot 83, is attached to suture anchor 65, and a pair of surgical needles 85A and 85B are attached to suture ends 80A and 80B, respectively. The working end of a representative suture anchor installation tool 90, of the sort described and illustrated in U S. patent application Ser. No. 07/308,318, is shown in FIG. 8 and generally comprises a hollow body 95 having a front end 100 and a side slot 105 for receiving barb 75 of suture anchor 65.

Further by way of illustration, in the preferred embodiment it is intended that the suture holding means 55 receive a suture such as the suture 80 attached to suture anchor 65, and the needle holding means 60 receive a pair of curved surgical needles such as the needles 85A and 85B shown attached to suture 80 in FIG. 7.

Figure 3:
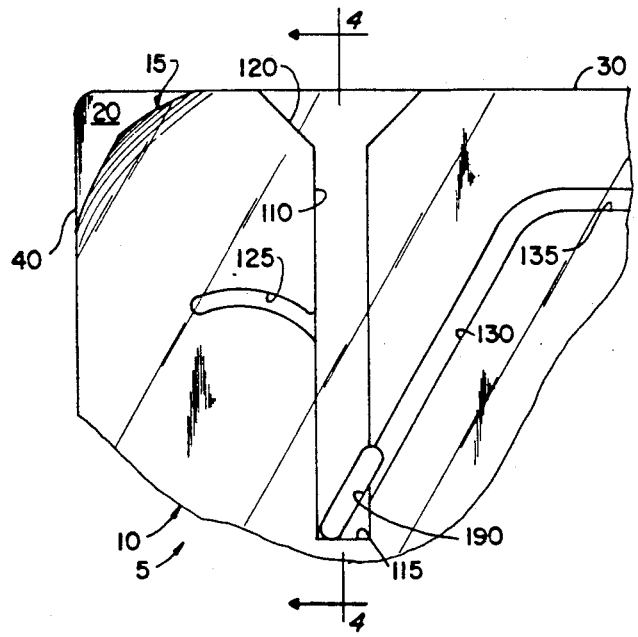
FIG. 3 is an enlarged side view showing the holder's suture anchor holding means in greater detail, with a portion of the holder's covering means having been drawn away from the holder's body.
Figure 4:
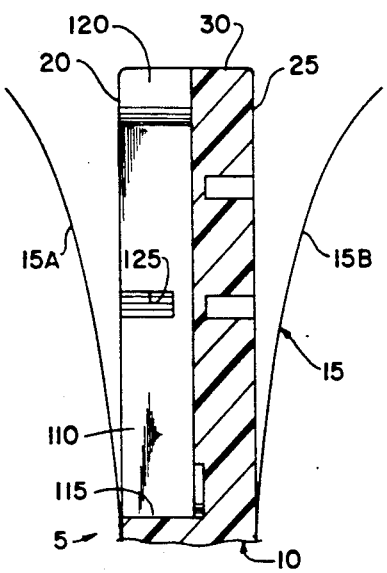
FIG. 4 is a sectional view taken along line 4—4 of FIG. 3, with portions of the holder's covering means having been drawn away from the holder's body.

To this end, and looking next at FIGS. 1, 3 and 4, suture anchor holding means 50 comprises a plurality of surface channels formed in left side surface 20 of body 10. More specifically, suture anchor holding means 50 comprises a surface channel 110 which opens on both left side surface 20 and top surface 30. Surface channel 110 extends parallel to front surface 40 and terminates in a bottom wall 115. Surface channel 110 is sized so as to receive the body 70 of suture anchor 65 (see FIG. 7) and to be able to accommodate the working end of the suture anchor installation tool 90 (FIG. 8) when it is brought into engagement with suture anchor 65, as will hereinafter be described in further detail. Surface channel 110 is chamfered at 120 where it adjoins top surface 30 so as to facilitate the insertion of installation tool 90 into surface channel 110 when the installation tool is moving into engagement with suture anchor 65, as will also hereinafter be described in further detail. Suture anchor holding means 50 also comprises a curved surface channel 125 which opens on left side surface 20 and communicates with surface channel 110. Curved surface channel 125 is sized so as to receive the barb 75 of suture anchor 65 when the body 70 of the suture anchor is received in surface channel 110, as will hereinafter be described in further detail.

Suture holding means 55 comprises a plurality of surface channels formed in left side surface 20, rear surface 45 and right side surface 25.

More specifically, suture holding means 55 comprises a surface channel 130 (FIG. 3) which is formed in left side surface 20 and communicates with surface channel 110, a surface channel 135 (FIGS. 1 and 3) which is formed in left side surface 20 and communicates with surface channel 130, and a surface channel 140 (FIGS. 1, 2 and 6) which is formed in rear surface 45 and communicates with surface channel 135.

Suture holding means 55 also comprises an archipelago-type recess 145 (FIG. 2) formed in right side surface 25 consisting of a plurality of islands 150 rising out of a common floor 155 and characterized by a surface channel 160, a series of parallel surface channels 165A, 165B, 165C, etc., and a surface channel 170. Islands 150 have their upper surfaces coplanar with right side surface 25. Surface channel 160 communicates with surface channel 140 formed in rear surface 45 and with recess 145, and surface channel 170 communicates with recess 145.

Suture holding means 55 also comprises a surface channel 175 (FIGS. 1, 2 and 6) which is formed in rear surface 45 and which communicates with surface channel 170, and a surface channel 180 (FIG. 1) which is formed in left side surface 20 and communicates with surface channel 175, and a pair of bifurcating surface channels 185A and 185B which are formed in left side surface 20 and which communicate with surface channel 180 and with one another.

Suture holding means 55 also comprises a deep channel 190 (FIG. 3) which is formed in the bases of surface channels 110 and 130.

Suture holding means 55 are sized to accommodate the suture 80 of suture anchor 65, as will hereinafter be described in further detail. It is to be appreciated that deep channel 190 is positioned to receive the suture knot 83 when the body 70 of suture anchor 65 is received in surface channel 110, as will hereinafter be described in further detail.

Figure 2:
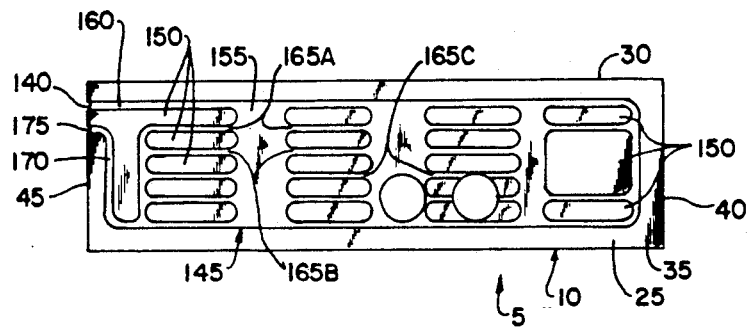
FIG. 2 is a side view in elevation showing the right side of the same holder.

Needle holding means 60 comprise a pair of semi-circular surface channels 195A and 195B (FIG. 1) which are formed in left side surface 20 and which communicate with bifurcating surface channels 185A and 185B, respectively. Needle holding means 60 also comprise a pair of through-holes 200A and 200B which extend completely through body 10 from left side surface 20 to right side surface 25 (FIGS. 1 and 2). Through-holes 200A and 200B communicate with semi-circular surface channels 195A and 195B, respectively. Needle holding means 60 serve to receive a pair of semi-circular surgical needles such as the surgical needles 85A and 85B attached to suture 80 (FIG. 7), and through-holes 200A and 200B permit the needles to be grasped by conventional needle graspers of the sort well known in the art while the needles are carried by body 10, as will hereinafter be described in further detail.

Looking next at FIGS. 3, 4 and 6, cover 15 is preferably formed out of a U-shaped piece of flexible transparent plastic such that it has a first section 15A which is normally positioned adjacent left side surface 20, a second section 15B which is normally positioned adjacent right side surface 25, and a third section 15C which is positioned adjacent to bottom surface 35. It is to be appreciated that third section 15C is attached securely to bottom surface 35 so that first section 15A is biased towards, but is free to move away from, left side surface 20, and second section 15B is biased towards, but is free to move away from, right side surface 25 (FIG. 4). It is an important aspect of the present invention that at least cover sections 15A and 15B, and possibly also body member 10, be formed out of a transparent material, whereby the user will be able to observe the status of the suture anchor assembly carried by holder 5 at all times.

Alternatively, cover 15 could also be formed out of just the two sections 15A and 15B, with the third section 15C omitted, with the two sections 15A and 15B being attached to the side surfaces 20 and 25, respectively, near where side surfaces 20 and 25 meet bottom surface 35, such that the top ends of cover sections 15A and 15B are normally biased towards side surfaces 20 and 25, respectively, but are also free to move away from side surfaces 20 and 25, respectively, in response to appropriate urging to do the same.

It is an important aspect of the present invention that cover 15 normally cover suture anchor holding means 50, suture holding means 55 and needle holding means 60, but be free to move away from body 10 to expose the same upon the appropriate urging to do the same.

Holder 5 is used as follows.

First, a suture anchor assembly, consisting of at least a suture anchor and a suture attached to the suture anchor, and preferably also at least one surgical needle attached to the suture, are attached to the holder. This is done by urging cover 15 away from body 10 if cover 15 has already been attached to body 10 so as to expose suture anchor holding means 50, suture holding means 55 and needle holding means 60, and then placing the suture anchor in suture anchor holding means 50, placing the suture in the suture holding means 55 and, if one or more surgical needles are provided as part of the suture anchor assembly, by placing the surgical needle(s) in the needle holding means 60.

By way of example, in the situation where holder 5 is adapted to hold a suture anchor assembly such as that consisting of a suture anchor 65 and a suture 80 and needles 85A and 85B (FIG. 7), and where the suture anchor is adapted to be deployed using a suture anchor installation tool 90 (FIG. 8), cover sections 15A and 15B would be urged away from side surfaces 20 and 25, respectively, to expose the various surface channels making up suture anchor holding means 50, suture holding means 55 and needle holding means 60. Suture anchor 65 would be positioned so that its body 70 is positioned in surface channel 110 and its barb 75 positioned in surface channel 125. In this regard, it is to be appreciated that the surface channels 110 and 125 making up the suture anchor holding means 50 are sized, relative to suture anchor 65, so that the suture anchor makes a slight friction fit with the surrounding walls of holder 5 so as to keep the suture anchor lightly in place. See FIG. 9.

At the same time, the suture anchor assembly's suture 80 would be positioned in suture holding means 55 by threading the two strands of suture 80A and 80B into surface channel 130 (FIG. 1), along surface channel 135, around the rear of holder 5 via surface channel 140 (FIG. 6), into archipelago recess 145 via channel 160 (FIG. 2), around islands 150 and into parallel channels 165A, 165B, 165C, etc., then back out archipelago recess 145 via channel 170, back around the rear of the holder 5 via surface channel 175 (FIG. 6), and then down the left side of holder 5 via surface channel 180 (FIG. 1). Suture ends 85A and 85B are then loaded into bifurcated channels 185A and 185B, respectively. It is to be appreciated that the surface channels making up the suture receiving means 55 are sized, relative to suture 80, so that the suture makes a slight friction fit with the surrounding walls of holder 5 so as to keep the suture lightly in place. It is also to be appreciated that a sufficient number of windings are made around islands 150 in archipelago recess 145 to ensure that substantially all of the suture material is deployed in the surface channels making up suture receiving means 55. It is also to be appreciated that suture knot 83 (FIG. 7) will be received in deep channel 190 (FIG. 2) when suture anchor 65 is deployed in suture anchor holding means 50 and suture 80 is deployed in suture holding means 55. See FIGS. 9 and 10.

Furthermore, needles 85A and 85B are positioned in needle holding means 60 by pressing needle 85A into surface channel 195A and by pressing needle 85B into surface channel 195B. It is to be appreciated that in the preferred embodiment, the surface channels 195A and 195B making up the needle receiving means 60 are sized and shaped, relative to needles 85A and 85B, so that the needles make a slight friction fit with the surrounding walls of holder 5, thereby keeping the needles lightly in place in the holder. By way of example, surface channels 195A and 195B may be formed with a slightly different radius of curvature than needles 85A and 85B, and the needles bent slightly while being loaded into channels 195A and 195B, so that the natural spring of the needles will keep them lightly engaged with the surrounding walls of holder 5. See FIGS. 9 and 10.

It is to be appreciated that the various surface channels making up suture anchor holding means 50, suture holding means 55 and needle holding means 60 are all sized, relative to the component members of the suture anchor assembly, such that the component members will be held by holder 5 beneath the planes of side surfaces 20 and 25, whereby cover sections 15A and 15B will be able to lie flush with side surfaces 20 and 25, respectively, when the suture anchor assembly is loaded on the holder 5.

As noted above, if cover 15 has been attached to body 10 before the suture anchor assembly has been mounted on body 10, cover 15 must have its two sections 15A and 15B urged away from side surfaces 20 and 25, respectively, so as to expose suture anchor holding means 50, suture holding means 55 and needle holding means 60 for loading with the respective parts of the suture anchor assembly. Preferably, however, the suture anchor assembly is mounted to the holder's body 10 before cover 15 is attached to body 10. In this way the necessary surfaces of body 10 will be readily exposed for receiving the various portions of the suture anchor assembly without cover 15 getting in the way during loading.

In any case, it will be appreciated that once the suture anchor assembly has been mounted to holder 5 and cover portions 15A and 15B allowed to take their natural positions adjacent body surfaces 20 and 25, respectively, the cover portions 15A and 15B will form protective covers which will not only help hold the suture anchor assembly to body 10, but also protect and shield the suture anchor assembly while it is mounted to holder 5. At the same time, it will be appreciated that cover portions 15A and 15B may be forced away from holder side surfaces 20 and 25 as needed so as to allow the various portions of the suture anchor assembly to be removed from the holder when desired. Furthermore, inasmuch as at least cover portions 15A and 15B are transparent, and possibly body 10 as well, the user handling holder 5 will be able to visually determine the condition of the suture anchor assembly at all times while any of its component parts are carried by the holder.

Once the suture anchor assembly has been loaded onto holder 5 in the foregoing manner, it may be sterilized and packaged. It is to be appreciated that a suture anchor installation tool 90 may be packaged in the same package, or it may be packaged in another independent package.

Thereafter, when it is desired to use the suture anchor assembly in a surgical procedure, the holder 5 (carrying the suture anchor assembly) is removed from its package, as is the suture anchor installation tool 90. Then the suture anchor is loaded onto the installation tool. This is done by pressing the leading end 110 of the suture anchor installation tool into surface channel 110 from top surface 30 so that the leading end of the installation tool enters channel 110 and engages the suture anchor so that a portion of the suture anchor is received within the interior of the installation tool and the anchor's barb 75 extends out through the tool's slot 105, in the manner taught in U.S. patent application Ser. No. 07/308,318. It is to be appreciated that the entry of installation tool 90 into channel 110 is assisted by the chamfering 120 provided where surface channel 110 opens on top surface 30.

Once the suture anchor has been loaded on the installation tool, the installation tool is moved so that the suture anchor is lifted up, out of surface channels 110 and 125, and freed from holder 5. It is to be appreciated that as this is done, cover portion 15A will be easily pushed away from the holder's left side surface 25 to allow the suture anchor to depart the holder.

As the suture anchor is carried away from the holder by the installation tool, the suture 80 will be played out from the holder's suture holding means 55. As this occurs, cover portions 15A and 15B press towards side surfaces 20 and 25, respectively, and thereby provide some resistance to the passage of the suture through the space between cover portions 15A and 15B and side surfaces 20 and 25, respectively. This resistance to the passage of the suture has the effect of controlling the release of the suture from the holder, while still allowing the suture to depart from the holder under direct urging to do so. At the same time, cover portion 15A will also provide an effective shield against the user inadvertently coming into contact with any sharp needles carried by the holder.

Next, after the suture anchor has been deployed in the body and it is desired to use needles 85A and 85B to suture something in place, cover portion 15A is manually pulled away from holder side surface 20 to expose the needles in the needle holding means 60. Then a conventional needle grasper (not shown) is used to grasp one needle at a time and pull it out of its seat on holder 5. It is to be appreciated that through-holes 200A and 200B will provide excellent access to the full width of the needle during this grasping procedure. The needles may then be used as desired.

It is, of course, to be appreciated that certain changes may be made to the foregoing embodiment without departing from the scope of the present invention.

Thus, for example, the holder could be used in conjunction with a suture anchor assembly consisting of only a suture anchor and a suture, and which omits the at least one surgical needle. In such a circumstance the needle holding means 60 could be omitted from the holder, or the needle holding means 60 could be provided but simply left unfilled.

Furthermore, it is anticipated that holders could be provided which would accept suture anchors having different geometries than the suture anchor disclosed in FIG. 7. In such a circumstance, the holder's body 10 would have its outer surfaces cut away in various locations so as to form suture anchor holding means for releasably holding such an alternative suture anchor to the holder, with the suture anchor holding means comprising one or more channels formed in at least one outer surface of body 10 which reflect the profile of the particular suture anchor which is to be received by the holder.

By way of example, a holder could be provided which is adapted to receive a suture anchor of the sort having more than one barb, e.g. a suture anchor of the sort having two barbs extending out of one of its ends, wherein the barbs extend in diametrically opposed directions, or a suture anchor of the sort having three barbs extending out of one of its ends, such as the suture anchor shown in FIGS. 11 and 12 of U.S. Pat. No. 4,898,156. Or a holder could be provided which is adapted to receive a suture anchor having an entirely different geometry. Whatever the case, in such a circumstance the holder's body 10 would have its outer surfaces cut away in various locations so as to form appropriate suture anchor holding means for holding such an alternative suture anchor to the holder, wherein the suture anchor holding means comprise one or more channels formed in at least one outer surface of body 10, the one or more channels reflecting the profile of the particular suture anchor which is to be received by the holder.

Furthermore, it is envisioned that through-holes 200A and 200B, which are provided to permit access to surgical needles 85A and 85B, might be replaced with deep blind holes which, while having their bases set lower than the bases of semi-circular surface channels 195A and 195B, terminate short of right side surface 25.

In addition, while in the embodiment disclosed herein it was indicated that the suture anchor holding means 50, the suture holding means 55 and the needle holding means 60 were all sized and/or shaped so as to make a slight friction fit with the components of the suture anchor assembly received therein, such slight friction fit helping to hold the components in place in the holder, it is also anticipated that the suture anchor holding means 50, the suture holding means 55 and/or the needle holding means 60 could be sized so that they make no slight friction fit with the components received therein; in such a situation, cover 15 would serve to hold the various components of the suture anchor assembly to body 10.

Still other modifications will be obvious to persons skilled in the art.

ADVANTAGES OF THE INVENTION

Numerous advantages are achieved by using the present invention.

For one thing, a novel holder is provided in which a suture anchor assembly, comprising at least a suture attached to a suture anchor and preferably also comprising at least one surgical needle attached to the suture, can be maintained from the time of manufacture until at least after the time that the suture anchor is united with the suture anchor installation tool.

For another thing, a novel holder is provided which will hold the suture anchor of the suture anchor assembly and permit its position to be carefully controlled while the suture anchor is being united with the suture anchor installation tool.

And a novel holder is provided which will hold the suture of the suture anchor assembly and permit it to be maintained and then deployed in a carefully controlled manner so as to prevent any tangling of the suture before it is deployed in the body.

Also, a novel holder is provided which will hold the at least one surgical needle of the suture anchor assembly, if one is provided as part of the suture anchor assembly, and permit it to be maintained in a protected manner until it is needed by the physician.

Furthermore, a novel holder is provided which will hold a suture anchor assembly, comprising at least a suture attached to a suture anchor and preferably also at least one surgical needle attached to the suture, prior to unification of the suture anchor with the suture anchor installation tool, and in which the user can keep observe the condition of the suture anchor assembly the entire time that its components are carried by the holder.

Also, a novel holder is provided which can be used with a variety of different suture anchors and suture anchor assemblies.

Still other advantages will be obvious to persons skilled in the art.

What is claimed is:

1. A holder for holding a suture anchor assembly of the sort comprising a suture attached to a suture anchor, wherein said suture anchor is adapted to be united with a suture anchor installation tool and thereafter deployed in a body using said suture anchor installation tool, said holder comprising:

a body;

at least one planar outer surface formed on said body;

suture anchor holding means for releasably holding said suture anchor to said body, said suture anchor holding means being formed in said body and opening on said at least one planar outer surface and being adapted to present said suture anchor for engagement by said suture anchor installation tool;

suture holding means for releasably holding said suture to said body, said suture holding means being formed in said body and opening on said at least one planar outer surface; and covering means for selectively covering said suture anchor while said suture anchor is held by said suture anchor holding means, and for selectively covering substantially all of said suture while said suture is held by said suture holding means, said covering means being attached to said body and being biased against said at least one planar outer surface so as to normally cover said suture anchor while said suture anchor is held by said suture anchor holding means and thereby help hold said suture anchor in said suture anchor holding means, and cover said suture while said suture is held by said suture holding means and thereby help hold said suture in said suture holding means, said covering means being capable of being urged away from said at least one planar outer surface so as to expose said suture anchor and said suture.

2. A holder according to claim 1 wherein said suture anchor holding means comprises at least one surface channel formed in said body and opening on said at least one planar outer surface, said at least one surface channel being adapted to receive said suture anchor therein.

3. A holder according to claim 1 wherein said covering means comprises a sheet of plastic attached to said body at one portion of said sheet.

4. A holder for holding a suture anchor assembly of the sort comprising a suture attached to a suture anchor, wherein said suture anchor is adapted to be united with a suture anchor installation tool and thereafter deployed in a body using said suture anchor installation tool, said holder comprising:
  a body;
  a first planar outer surface formed on said body;
  a second planar outer surface formed on said body;
  suture anchor holding means for releasably holding said suture anchor to said body, said suture anchor holding means being formed in said body and opening on said first planar outer surface and being adapted to present said suture anchor for engagement by said suture anchor installation tool;
  suture holding means for releasably holding said suture to said body, said suture holding means being formed in said body and opening on said second planar outer surface; and
  covering means for selectively covering said suture anchor while said suture anchor is held by said suture anchor holding means, and for selectively covering substantially all of said suture while said suture is held by said suture holding means,
  said covering means being attached to said body and being biased against said first planar outer surface and said second planar outer surface so as to normally cover said suture anchor while said suture anchor is held by said suture anchor holding means and thereby help hold said suture anchor in said suture anchor holding means, and cover said suture while said suture is held by said suture holding means and thereby help hold said suture in said suture holding means, said covering means being capable of being urged away from said first planar outer surface so as to expose said suture anchor and said second planar outer surface so as to expose said suture.

5. A holder according to claim 4 wherein said suture anchor holding means comprises at least one surface channel formed in said body and opening on said first planar outer surface, said at least one surface channel being adapted to receive said suture anchor therein.

6. A holder according to claim 4 wherein said covering means comprises a sheet of plastic attached to said body at an intermediate portion of said sheet so that a first end portion of said sheet covers said first planar outer surface and a second end portion of said sheet covers said second planar outer surface.

7. A holder for holding a suture anchor assembly of the sort comprising a suture attached to a suture anchor and at least one needle attached to said suture, wherein said suture anchor is adapted to be united with a suture anchor installation tool and thereafter deployed in a body using said suture anchor installation tool, said holder comprising:
  a body;
  a first planar outer surface formed on said body;
  a second planar outer surface formed on said body;
  suture anchor holding means for releasably holding said suture anchor to said body, said suture anchor holding means being formed in said body and opening on said first planar outer surface and being adapted to present said suture anchor for engagement by said suture anchor installation tool;
  suture holding means for releasably holding said suture to said body, said suture holding means being formed in said body and opening on said second planar outer surface;
  needle holding means for releasably holding said at least one needle to said body, said needle holding means being formed in said body and opening on said first planar outer surface; and
  covering means for selectively covering said suture anchor while said suture anchor is held by said suture anchor holding means, and for selectively covering substantially all of said suture while said suture is held by said suture holding means, and for selectively covering said at least one needle while said at least one needle is held by said needle holding means;
  said covering means being attached to said body and being biased against said first planar outer surface and said second planar outer surface so as to normally cover said suture anchor while said suture anchor is held by said suture anchor holding means and thereby help hold said suture anchor in said suture anchor holding means, and cover said suture while said suture is held by said suture holding means and thereby help hold said suture in said suture holding means, and cover said at least one needle while said at least one needle is held by said needle holding means and thereby help hold said at least one needle in said needle holding means, said covering means being capable of being urged away from said first planar outer surface so as to expose said suture anchor and said at least one needle and said second planar outer surface so as to expose said suture.

8. A holder according to claim 7 wherein said suture anchor holding means comprises at least one surface channel formed in said body and opening on said first planar outer surface, said at least one surface channel being adapted to receive said suture anchor therein.

9. A holder according to claim 7 wherein said covering means comprises a sheet of plastic attached to said body at an intermediate portion of said sheet so that a first end portion of said sheet covers said first planar outer surface and a second end portion of said sheet covers said second planar outer surface.

10. An assembly comprising:
  (a) a suture anchor assembly comprising:
    a suture anchor; and
    a suture attached to said suture anchor; and
  (b) a holder for holding said suture anchor assembly, said holder comprising:
    a body;
    at least one planar outer surface formed on said body;
    suture anchor holding means for releasably holding said suture anchor to said body, said suture anchor holding means being formed in said body and opening on said at least one planar outer surface and being adapted to present said suture anchor for engagement by a suture anchor installation tool;
    suture holding means for releasably holding said suture to said body, said suture holding means being formed in said body and opening on said at least one planar outer surface; and
    covering means for selectively covering said suture anchor while said suture anchor is held by said suture anchor holding means, and for selectively covering substantially all of said suture while said suture is held by said suture holding means, said covering means being attached to said body and being biased against said at least one planar outer surface so as to normally cover said suture anchor while said suture anchor is held by said suture anchor holding means and thereby help hold said suture anchor in said suture anchor holding means, and cover said suture while said suture is held by said suture holding means and thereby help hold said suture in said suture holding means, said covering means being capable of being urged away from said at least one planar outer surface so as to expose said suture anchor and said suture.

11. An assembly according to claim 10 wherein said suture anchor holding means comprises at least one surface channel formed in said body and opening on said at least one planar outer surface, said at least one surface channel being adapted to receive said suture anchor therein.

12. An assembly according to claim 10 wherein said covering means comprises a sheet of plastic attached to said body at one portion of said sheet.

13. An assembly comprising:
   (a) a suture anchor assembly comprising:
      a suture anchor; and
      a suture attached to said suture anchor; and
   (b) a holder for holding said suture anchor assembly, said holder comprising:
      a body;
      a first planar outer surface formed on said body;
      a second planar outer surface formed on said body;
      suture anchor holding means for releasably holding said suture anchor to said body, said suture anchor holding means being formed in said body and opening on said first planar outer surface and being adapted to present said suture anchor for engagement by a suture anchor installation tool;
      suture holding means for releasably holding said suture to said body, said suture holding means being formed in said body and opening on said second planar outer surface; and
      covering means for selectively covering said suture anchor while said suture anchor is held by said suture anchor holding means, and for selectively covering substantially all of said suture while said suture is held by said suture holding means, said covering means being attached to said body and being biased against said first planar outer surface and said second planar outer surface so as to normally cover said suture anchor while said suture anchor is held by said suture anchor holding means and thereby help hold said suture anchor in said suture anchor holding means, and cover said suture while said suture is held by said suture holding means and thereby help hold said suture in said suture holding means, said covering means being capable of being urged away from said first planar outer surface so as to expose said suture anchor and said second planar outer surface so as to expose said suture.

14. An assembly according to claim 13 wherein said suture anchor holding means comprises at least one surface channel formed in said body and opening on said first planar outer surface, said at least one surface channel being adapted to receive said suture anchor therein.

15. An assembly according to claim 13 wherein said covering means comprises a sheet of plastic attached to said body at an intermediate portion of said sheet so that a first end portion of said sheet covers said first planar outer surface and a second end portion of said sheet covers said second planar outer surface.

16. An assembly comprising:
   (a) a suture anchor assembly comprising:
      a suture anchor;
      a suture attached to said suture anchor; and
      at least one needle attached to said suture; and
   (b) a holder for holding said suture anchor assembly, said holder comprising:
      a body;
      a first planar outer surface formed on said body;
      a second planar outer surface formed on said body;
      suture anchor holding means for releasably holding said suture anchor to said body, said suture anchor holding means being formed in said body and opening on said first planar outer surface and being adapted to present said suture anchor for engagement by a suture anchor installation tool;
      suture holding means for releasably holding said suture to said body, said suture holding means being formed in said body and opening on said second planar outer surface;
      needle holding means for releasably holding said at least one needle to said body, said needle holding means being formed in said body and opening on said first planar outer surface; and
      covering means for selectively covering said suture anchor while said suture anchor is held by said suture anchor holding means, and for selectively covering substantially all of said suture while said suture is held by said suture holding means, and for selectively covering said at least one needle while said at least one needle is held by said needle holding means;
      said covering means being attached to said body and being biased against said first planar outer surface and said second planar outer surface so as to normally cover said suture anchor while said suture anchor is held by said suture anchor holding means and thereby help hold said suture anchor in said suture anchor holding means, and cover said suture while said suture is held by said suture holding means and thereby help hold said suture in said suture holding means, and cover said at least one needle while said at least one needle is held by said needle holding means and thereby help hold said at least one needle in said needle holding means, said covering means being capable of being urged away from said first planar outer surface so as to expose said suture anchor and said at least one needle and said second planar outer surface so as to expose said suture.

17. An assembly according to claim 16 wherein said suture anchor holding means comprises at least one surface channel formed in said body and opening on said first planar outer surface, said at least one surface channel being adapted to receive said suture anchor therein.

18. An assembly according to claim 16 wherein said covering means comprises a sheet of plastic attached to said body at an intermediate portion of said sheet so that a first end portion of said sheet covers said first planar outer surface and a second end portion of said sheet covers said second planar outer surface.

19. A holder for holding a suture anchor assembly of the sort comprising a suture anchor and a suture attached to said suture anchor, wherein said suture anchor is adapted to be united with a suture anchor installation tool and thereafter deployed in a body using said suture anchor installation tool, said holder comprising:

a body having at least one outer surface;

suture anchor holding means for releasably holding said suture anchor to said body, said suture anchor holding means comprising a first groove formed in said body and opening on said at least one outer surface and being adapted to releasably receive said suture anchor and present said suture anchor for engagement by said suture anchor installation tool; and suture holding means for releasably holding said suture to said body, said suture holding means comprising a second groove formed in said body and opening on said at least one outer surface, said second groove being adapted to releasably receive said suture.

20. A holder according to claim 19 wherein said first and second grooves are connected to one another.

21. A holder according to claim 19 further including needle-holding means for releasably holding a needle attached to said suture, said needle-holding means comprising a third groove formed in said body and opening on said at least one outer surface, said third groove being adapted to releasably receive said needle.

22. A holder according to claim 21 wherein said third groove is connected to said second groove.

23. A holder according to claim 22 further including a fourth groove formed in said body and opening on said at least one outer surface, said fourth groove extending transversely of the length of said holder and terminating as an opening in a second outer surface of said body, with said second outer surface intersecting said first outer surface.

* * * * *